United States Patent [19]
Oonishi et al.

[11] Patent Number: 5,965,750
[45] Date of Patent: Oct. 12, 1999

[54] HIGH- PURITY TOCOPHEROL PHOSPHATES, PROCESS FOR THE PREPARATION THEREOF, METHODS FOR ANALYSIS THEREOF, AND COSMETICS

[75] Inventors: Yutaka Oonishi; Tsutomu Nozawa; Takami Ooe; Keisuke Mano; Naoaki Misu; Yohei Kurata, all of Kawasaki; Shinobu Ito; Eiji Ogata, both of Tokyo, all of Japan

[73] Assignee: Showa Denko K.K., Tokyo, Japan

[21] Appl. No.: 08/849,052

[22] PCT Filed: Oct. 17, 1996

[86] PCT No.: PCT/JP96/03015

§ 371 Date: May 29, 1998

§ 102(e) Date: May 29, 1998

[87] PCT Pub. No.: WO97/14705

PCT Pub. Date: Apr. 24, 1997

[30] Foreign Application Priority Data

Oct. 17, 1995 [JP] Japan .................................... 7-268798
Nov. 14, 1995 [JP] Japan .................................... 7-319500

[51] Int. Cl.$^6$ ..................................................... C07F 9/06
[52] U.S. Cl. ............................................................ 549/218
[58] Field of Search ............................................. 549/218

[56] References Cited

FOREIGN PATENT DOCUMENTS

| | | |
|---|---|---|
| 37-1737 | 5/1962 | Japan . |
| 64-70413 | 3/1969 | Japan . |
| 59-44375 | 3/1984 | Japan . |
| 59-219295 | 12/1984 | Japan . |
| 62-205091 | 9/1987 | Japan . |
| 2-111722 | 4/1990 | Japan . |

OTHER PUBLICATIONS

Yakugaku Zasshi, "Synthesis of Water–soluble Vitamin E Derivatives," Nakagawa et al., 75(11), 1322, 1955, pp. 1322–1325.

Chemical Pharmacy Bulletin, "A New Phosphorylating Reagent., The Preparation of the Mixed phosphoric . . . " Mushika et al., vol. 19, No. 4. 1971, pp. 687–695.

Pharmaceutical Chemistry Journal, (Khim. Farm. Zh. 17(7), 840, 1983), "Methods of Synthesis and Technology of Drug Production," 1797), 501, 1983 (English Trans.) pp. 501–504.

Bioact. Mol 3., "Synthesis of Vitamin E Phosphate and Vitamin $K_1$ Phosphate," from 2nd Intern' Symposium on Phosphrus Chemistry Directed Towards Biology., 1987, pp. 235–246.

*Primary Examiner*—Amelia Owens
*Attorney, Agent, or Firm*—Sughrue, Mion, Zinn Macpeak & Seas, PLLC

[57] ABSTRACT

Disclosed herein are a highly purified tocopheryl phosphate and/or a salt thereof (tocopheryl phosphates) wherein a P,P'-bistocopheryl hypophosphate and/or a salt thereof (P,P'-bistocopheryl diphoshates) is contained in a proportion of not higher than 3% by weight; a process for producing a highly purified tocopheryl phosphate and/or a salt thereof, which comprises the steps of reacting a tocopherol with an oxyphosphorus trihalide followed by treating with an acid or basic aqueous solution to thereby form tocopheryl phosphates (i) in which P,P'-bistocopheryl diphoshates (ii) formed as by-products are contained, hydrolyzing the P,P'-bistocopheryl diphoshates (ii) under acid condition, and, optionally, rendering the hydrolyzate neutral or basic under basic condition; and a method of analyzing tocopheryl phosphates, comprising analyzing a sample containing components (i) and (ii) with the use of a high-performance liquid chromatograph column packed with a gel of a polymethacrylate having, bonded thereto, long-chain alkyl groups. None or only an extremely minute amount of P,P'-bistocopheryl diphoshates are contained in the highly purified tocopheryl phosphates, so that the highly purified tocopheryl phosphates exhibit antioxidant and blood circulation promoting effects, have excellent water solubility, are powdery so that the handling thereof is extremely easy, are free from cutaneous irritation and allergenecity and ensure dermal safety. Therefore, the highly purified tocopheryl phosphates are useful as cosmetic ingredients. The amounts of components (i) and (ii) can be simply measured with high accuracy by the above method.

6 Claims, 2 Drawing Sheets

HIGH-PURITY TOCOPHEROL PHOSPHATES, PROCESS FOR THE PREPARATION THEREOF, METHODS FOR ANALYSIS THEREOF, AND COSMETICS

TECHNICAL FIELD

The present invention relates to highly purified tocopheryl phosphates which are soluble in water at about neutrality, a process for producing the same and a method of analyzing tocopheryl phosphates. The present invention also relates to cosmetics containing the above tocopheryl phosphates.

BACKGROUND ART

The tocopherol is generally well known as vitamin E. The tocopherol is much contained in vegetable oils such as peanut oil and soybean oil.

The vitamin E, i.e., tocopherol has been studied for the elucidation of the antisterile effect thereof. What has attracted the greatest interest during the study is the antioxidant effect of tocopherol. Further, extensive biologic effects have recently been recognized of tocopherols inclusive of tocopherol and salts thereof.

These effects of the tocopherols have been noted and, now, the tocopherols are used in a wide range of application fields such as not only pharmaceutical preparations, cosmetic ingredients and livestock feed additives but also food, health food and plastic additives.

However, the tocopherols have drawbacks in that they are insoluble in water although being soluble in fats and oils and organic solvents such as acetone and ethanol and are viscous and oily, so that the handling thereof is restricted and that they are easily oxidized by the action of light, heat, alkali, etc. in the air.

Accordingly, in recent years, extensive studies are made on, for example, converting the tocopherol to derivatives in order to increase the hydrophilicity thereof. Examples of such attempts to increase hydrophilicity of the tocopherol include the synthesis of a phosphoric diester of tocopherylglycerol and a salt thereof (see Japanese Patent Laid-open Publication No. 6(1994)-87875), the synthesis of a tocopherol glycoside (see, for example, Japanese Patent Laid-open Publication No. 60(1985)-56994) and the synthesis of an ethylene glycol derivative of tocopheryl phosphate (see Yakugaku Zasshi, 75, 1322 (1955) and Chem. Pharm. Bull., 19, 687 (1971)). Further, examples of the above attempts include the synthesis of a phosphoric diester of L-ascorbic acid/dltocopherol (see Japanese Patent Laid-open Publication Nos. 59(1984)-219295, 62(1987)-205091 and 02(1990)-111722).

However, all the tocopherol derivatives disclosed in the above literature must be synthesized through multiple stages of reactions, so that the problems are encountered that the production involves difficulty and the cost is high.

Moreover, an aqueous emulsion composition containing a tocopherol in high concentration has been proposed in Japanese Patent Publication No. 7(1995)-037381, which specifically contains an alkali metal salt of hemisuccinic ester of tocopheryl phosphate but contains none of a dissolution auxiliary and an emulsifier. Further, tocopheryl nicotinates have been proposed (see, for example, Japanese Patent Publication No. 55(1980)-049074).

However, the compounds described in these literature, like those described in the above literature, must be synthesized through multiple stages of reactions, so that the problems are encountered that the production involves difficulty and the cost is high. Further, they are scarcely soluble in water, so that the problem is encountered that the addition thereof to a wide variety of cosmetic preparations is difficult.

It has been reported that a sodium salt of tocopheryl phosphate is a hydrophilic tocopherol derivative whose synthesis is relatively easy (see Yakugaku Zasshi, 75, 1322 (1955), Japanese Patent Publication Nos. 37(1962)-1737 and 03(1991)-32558 and Khim.-Fram. Zh., 17(7), 840 (1983)).

However, Nakagawa et al. have described in the pharmaceutical journal (Yakugaku Zasshi, 75(11), 1322 (1955)) that an aqueous solution of tocopheryl phosphate obtained by the reaction of tocopherol with an oxyphosphorus trichloride is emulsified, when brought into about neutrality, or form precipitates, which are not readily soluble in water.

E. E. Zhukova et al. have described in the journal (Khim.-Fram. Zh., 17(7), 840 (1983)) that a tocopheryl phosphate can be obtained by reacting an oxyphosphorus trichloride substituted with a protective group with a tocopherol and removing the protective group but the yield is low and that only a disodium salt is soluble in water, that is, the tocopheryl phosphate is soluble only at a basicity of at least 10 in pH.

The inventors have made extensive studies with a view toward solving the above problems. As a result, it has been found that the alkali metal of tocopheryl phosphate is emulsified or precipitated at about neutrality for the following reason.

That is, it has been found that when an oxyphosphorus trihalide is reacted with a tocopherol in the presence of a deacidation agent such as pyridine and the phosphorushalogen bond of the reaction product is hydrolyzed, not only is the tocopheryl phosphate obtained but also an impurity of P,P'-bistocopheryl diphosphate is formed as a by-product. It has further been found that this P,P'-bistocopheryl diphosphate has a low solubility in a neutral aqueous solution, so that a solid is precipitated from an aqueous solution in which a certain level of the P,P'-bistocopheryl diphosphate is contained, thereby causing clouding and precipitation.

The inventors have made further extensive studies on the basis of the above finding. As a result, it has been found that an aqueous solution of tocopheryl phosphates which is clear at neutrality can be obtained either by performing a specified treatment of the above mixture of tocopheryl phosphate and P,P'-bistocopheryl diphosphate under specified conditions to thereby effect a selective decomposition of the P,P'-bistocopheryl diphosphate or by reacting a tocopherol with an oxyphosphorus trihalide and, thereafter, treating the reaction mixture by a specified method so that the tocopheryl phosphate is produced under conditions such that none of P,P'-bistocopheryl diphosphate is formed or the formation thereof is minimized. The present invention has been completed on the basis of this finding.

In connection with the cosmetic, the conventional preparations containing tocopheryl phosphates and process for producing the same have involved the following problems.

That is, the addition of the tocopheryl phosphate and/or salt thereof which has been produced by the conventional synthetic method to a cosmetic has involved the problem that the tocopheryl phosphate or salt thereof is soluble to an appreciable degree in an alkali aqueous solvent but scarcely soluble in a nearly neutral aqueous solvent of 5 to 9 in pH which is commonly employed in cosmetic use, so that the addition thereof to a wide variety of cosmetic preparations is difficult. In particular, the addition of the tocopheryl phosphate which has been produced by the conventional synthetic method to a cosmetic having a high water content such as toilet water which is a mainstream of the recent cosmetic has involved the problem that troubles such as changing of viscosity, breaking of emulsification and precipitation of insoluble matter in the preparation with the passage of time occur to thereby gravely deteriorate the quality of the cosmetic.

The method in which, for example, a nonionic surfactant is added to the tocopheryl phosphate to thereby emulsify and disperse the same as mentioned hereinbefore (see Japanese Patent Publication No. 03(1991)-32558) is known as means for solving the above problems. However, this method has drawbacks in that an additional emulsification step must be provided to thereby complicate the process and that an emulsion type cosmetic results to thereby cause heavy feeling and disenable production of a transparent toilet water which is a mainstream of the recent cosmetic. Further, the problem has been encountered that a cosmetic preparation whose time stability is satisfactory from the viewpoint of a stability test over a period as long as three years at room temperature, a stability test at about neutrality and an accelerated test at 40° C. which cosmetics should pass cannot be obtained.

In contrast, the above process for producing highly purified tocopheryl phosphates and the highly purified tocopheryl phosphates produced by this process, which have been completed by the inventors, are advantageous over the prior art in that the amount of impurities is very small and the tocopheryl phosphates have high solubility, do not form precipitates at neutrality irrespective of the passage of time and can suitably be added to cosmetics.

In the prior art process, as mentioned above, the tocopheryl phosphate is produced by reacting an oxyphosphorus trihalide with a tocopherol in the presence of pyridine and hydrolyzing the phosphorus-halogen bond of the reaction product in alkali condition. That the formation of not only the tocopheryl phosphate but also an impurity of P,P'-bistocopheryl diphosphate is inevitable in this prior art process has been confirmed by an analytical method for impurities made by the present inventors.

As a result of the inventors' studies, it has been found that the P,P'-bistocopheryl diphosphate has poor solubility in water, especially low solubility in water at neutrality of 5 to 9 in pH, so that the addition thereof to cosmetics would cause the P,P'-bistocopheryl diphosphate to crystallize in the preparation with the passage of time to thereby form precipitates.

Therefore, it is required to control the content of P,P'-bistocopheryl diphoshate and, accordingly, to establish the method of measuring the quantity thereof and develop means for selectively decomposing and removing the P,P'-bistocopheryl diphoshate, for obtaining the cosmetic preparation of tocopheryl phosphate which is stable at neutrality.

It is common to conduct an analysis of tocopheryl phosphates in most cases by ultraviolet/visible radiation spectroscopy or $^{31}$P-NMR (see, for example, Bioact. Mol., 3, 235 (1987)). With the use of such an analytical method, however, it has been difficult to determine the ratio of content of tocopheryl phosphate to P,P'-bistocopheryl diphoshate when the P,P'-bistocopheryl diphoshate is contained in a sample only in an amount of as small as about a few percents. Further, the content of a compound containing no phosphorus atoms such as tocopherol as a starting material cannot be measured by such an analytical method, and there has been the problem that the preparation of an analytical sample and the measurement thereof consume a relatively large amount of workload and time. Thus, there is no method for obtaining a highly purified tocopheryl phosphate on the basis of an accurate measurement of the content of such impurities. The use of the tocopheryl phosphate obtained in the prior art invites the mixing of impurities into the cosmetic to thereby not only threaten the safety of the cosmetic but also cause the danger of deterioration of the quality of the cosmetic preparation, especially, occurrence of sediments with the passage of time. Therefore, the use of tocopheryl phosphates as cosmetic ingredients has been under extensive restraints.

The inventors have solved these problems and have also completed an analytical method which enables readily detecting tocopheryl phosphates and measuring the content thereof with high precision.

OBJECT OF THE INVENTION

The present invention is intended to solve the above problems of the prior art, and it is an object of the present invention to provide a highly purified tocopheryl phosphate and/or salt thereof which is soluble in water at about neutrality and highly stable (hereinafter collectively also referred to as "tocopheryl phosphates") and a process for producing the same.

It is another object of the present invention to provide a cosmetic containing tocopheryl phosphates which is free from precipitation of solid matter such as impurities and ensures high solubility in water and high preparation stability.

It is a further object of the present invention to provide a simple analytical method which enables measuring the content of each ingredient in cosmetics and various samples containing not only tocopheryl phosphates but also an impurity of P,P'-bistocopheryl diphoshate and/or salt thereof (hereinafter collectively also referred to as "P,P'-bistocopheryl diphoshates") and enables determining the purity of articles containing tocopheryl phosphates.

SUMMARY OF THE INVENTION

In one aspect of the present invention, there is provided a highly purified tocopheryl phosphate and/or a salt thereof (highly purified tocopheryl phosphates) wherein a P,P'-bistocopheryl diphoshate and/or a salt thereof is contained in a proportion of not higher than 3% by weight, preferably, not higher than 2% by weight and, still preferably, not higher than 0.5% by weight.

The highly purified tocopheryl phosphates of the present invention, wherein an aqueous solution formed therefrom having a concentration of 3% by weight with a pH value of 8.5, are clear or substantially clear.

In the highly purified tocopheryl phosphates of the present invention, it is preferred that the salt of tocopheryl phosphate contained therein is present in the form of a sodium salt or a potassium salt.

In another aspect of the present invention, there is provided a process for producing highly purified tocopheryl phosphates, which comprises hydrolyzing under acid condition a mixture of:

a tocopheryl phosphate and/or a salt thereof (i) and a P,P'-bistocopheryl diphoshate and/or a salt thereof (ii).

In a further aspect of the present invention, there is provided a process for producing highly purified tocopheryl phosphates, which comprises the steps of:

reacting a tocopherol with an oxyphosphorus trihalide and treating the reaction mixture with an acid or basic aqueous solution to thereby form a tocopheryl phosphate and/or a salt thereof in which a P,P'-bistocopheryl diphoshate and/or a salt thereof formed as a by-product is contained, hydrolyzing the P,P'-bistocopheryl diphoshate and/or salt thereof under acid condition, and, optionally, rendering the hydrolyzate neutral or basic under basic condition (basic aqueous solution).

The cosmetic of the present invention comprises the above highly purified tocopheryl phosphates. This cosmetic may further comprise an ascorbic acid derivative and/or a salt thereof. In this cosmetic, it is preferred that the salt of tocopheryl phosphate contained in the highly purified tocopherol phosphate is present in the form of a sodium salt or a potassium salt in the highly purified tocopheryl phosphates.

In still a further aspect of the present invention, there is provided a method of analyzing tocopheryl phosphates, comprising analyzing a sample containing:

a tocopheryl phosphate and/or a salt thereof (i) and a P,P'-bistocopheryl diphoshate and/or a salt thereof (ii), with the use of a high-performance liquid chromatograph column packed with a gel of a polymethacrylate having, bonded thereto, long-chain alkyl groups, preferably, octadecyl groups.

In the method of the present invention, it is preferred that the column temperature is 38 to 42° C. and the analysis is conducted with the use of a 100/0.9 to 100/1.1 (volume ratio) mixture of methanol/water containing 0.04 to 0.06 M (mol/liter) sodium acetate as an eluate and with the use of a spectrophotometer for ultraviolet and visible region as a detector.

None or only an extremely minute amount of P,P'-bistocopheryl diphoshates are contained in the above highly purified tocopheryl phosphate and/or salt thereof according to the present invention (highly purified tocopheryl phosphates). The highly purified tocopheryl phosphates exhibit antioxidant and blood circulation promoting effects and have excellent water solubility. The aqueous solution of highly purified tocopheryl phosphates having a concentration of 3% by weight with a pH value of 8.5, are clear or substantially clear. Moreover, the highly purified tocopheryl phosphates are powdery so that the handling thereof is extremely easy, are free from cutaneous irritation and allergenecity and ensure dermal safety. Therefore, the highly purified tocopheryl phosphates are useful as cosmetic ingredients.

In the present invention, the terminology "clear or substantially clear" refers to clarity evaluated in accordance with the criteria described on pages 1312–1313, general rule, commentary II, 2nd edition of "Japanese Standards of Cosmetic Ingredients" edited by Society of Japanese Pharmacopoeia and published by Yakuji Nippo, Ltd. in 1984.

In the present invention, use is made of a column packed with a gel of a polymethacrylate having, bonded thereto, long-chain alkyl groups, preferably, octadecyl groups as mentioned above, by which the content of P,P'-bistocopheryl diphoshate in a sample can be measured more simply and more accurately than in the conventional analytical method.

DETAILED DESCRIPTION OF THE INVENTION

Figure 1:
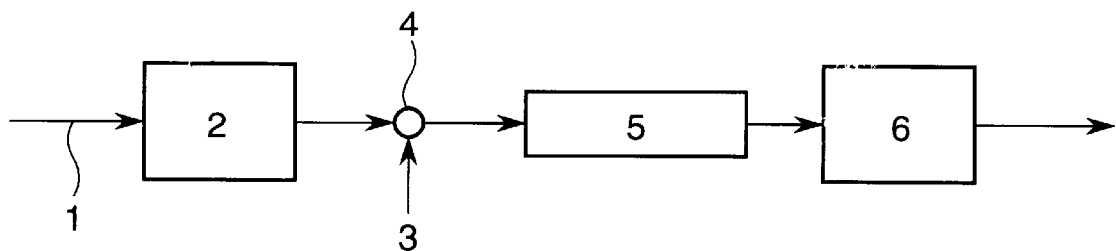
FIG. 1 is a system diagram showing the construction of the analyzer of the present invention.

First, the highly purified tocopheryl phosphate and/or salt thereof (highly purified tocopheryl phosphates) according to the present invention and the process for producing the same will be described below.

Highly Purified Tocopheryl Phosphate and/or salt thereof

The highly purified tocopheryl phosphates of the present invention comprise at least 97% by weight, preferably, at least 98% by weight and, still preferably, at least 99.5% by weight of the tocopheryl phosphate, for example, represented by the below shown formula [I] and/or salt thereof (i). The lower the content of the P,P'-bistocopheryl diphoshate, for example, represented by the below shown formula [II] and/or salt thereof (ii) (P,P'-bistocopheryl diphoshates), the more desirable. The ontent of P,P'-bistocopheryl diphoshates in the highly purified tocopheryl phosphates is 3% by weight or below, preferably, 2% by weight or below and, still preferably, 0.5% by weight or below, provided that the total of the tocopheryl phosphates (i) and P,P'-bistocopheryl diphoshates (ii) is 100% by weight.

When the content of P,P'-bistocopheryl diphoshates as impurities in a tocopheryl phosphates containing material exceeds 3% by weight, it is likely that the solubility of the material in an aqueous solvent with a pH value of about 5 to 9 becomes poor and clouding and precipitation occur with the passage of time to thereby cause the addition of the material to a wide variety of cosmetics to be difficult.

It is preferred that an aqueous solution of the highly purified tocopheryl phosphate and/or salt thereof be clear or substantially clear from the viewpoint, for example, that the application to a wide variety of cosmetics, drugs, livestock feed additives, foods (including health foods), etc. can be facilitated.

The above tocopheryl phosphate is represented by, for example, the following formula:

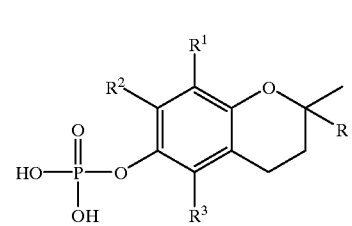

[I]

In the formula [I], each of $R^1$ to $R^3$ independently represents a methyl group or a hydrogen atom, and R represents $C_{16}H_{33}$ or $C_{16}H_{27}$. When R is $C_{16}H_{33}$ (tocopherol type), it is represented by, for example, the formula:

(r-1)

On the other hand, when R is $C_{16}H_{27}$ (tocotrienol type), it is represented by, for example, the formula:

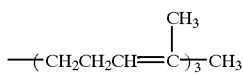

(r-2)

Examples of the tocopheryl phosphates represented by the formula [I] include α-, β-, γ- and δ-tocopheryl phosphates and α-, β-, γ- and δ-tocotrienyl phosphates.

Salts of the above tocopheryl phosphates are, for example, alkali metal, alkaline earth metal and ammonium salts of the tocopheryl phosphates. Specific examples thereof include alkali metal, alkaline earth metal and ammonium salts of α-, β-, γ- and δ-tocopheryl phosphates and alkali metal, alkaline earth metal and ammonium salts of α-, β-, γ- and δ-tocotrienyl phosphates.

The above P,P'-bistocopheryl diphoshate is represented by, for example, the following formula:

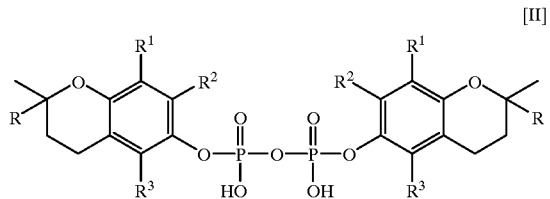

[II]

In the formula [II], each of $R^1$ to $R^3$ independently represents a methyl group or a hydrogen atom, and R represents $C_{16}H_{33}$ or $C_{16}H_{27}$ as mentioned above.

Examples of the P,P'-bistocopheryl diphosphates represented by the formula [II] include P,P'-bis-α-, β-, γ- and δ-tocopheryl hypophosphates and P,P'-bis-α-, β-, γ- and δ-tocotrienyl hypophosphates.

Salts of the above P,P'-bistocopheryl diphoshates are, for example, alkali metal, alkaline earth metal and ammonium salts of the tocopheryl phosphates. Specific examples thereof include alkali metal, alkaline earth metal and ammonium salts of P,P'-bis-α-, β-, γ- and δ-tocopheryl hypophosphates and alkali metal, alkaline earth metal and ammonium salts of P,P'-bis-α-, β-, γ- and δ-tocotrienyl hypophosphates.

None or, if any, only an extremely minute amount (3% by weight or below, preferably, 2% by weight or below and, still preferably, 0.5% by weight or below in highly purified tocopheryl phosphates) of P,P'-bistocopheryl diphoshates are contained in the above highly purified tocopheryl phosphates according to the present invention. The highly purified tocopheryl phosphates exhibit antioxidant and blood circulation promoting effects and have excellent water solubility. Moreover, the highly purified tocopheryl phosphates are powdery so that the handling thereof is extremely easy and, as described below, are free from cutaneous irritation and allergenecity and ensure dermal safety. Therefore, the highly purified tocopheryl phosphates are useful as cosmetic ingredients.

Now, the process for producing the above highly purified tocopheryl phosphates will be described in the order of individual steps thereof.

Production of Highly Purified Tocopheryl Phosphates

In a mode of the process of the present invention, referring to the following formula, a tocopherol (1) is first reacted with an oxyphosphorus trihalide (2), thereby obtaining a oxyphosphorus dihalide compound of tocopherol (3):

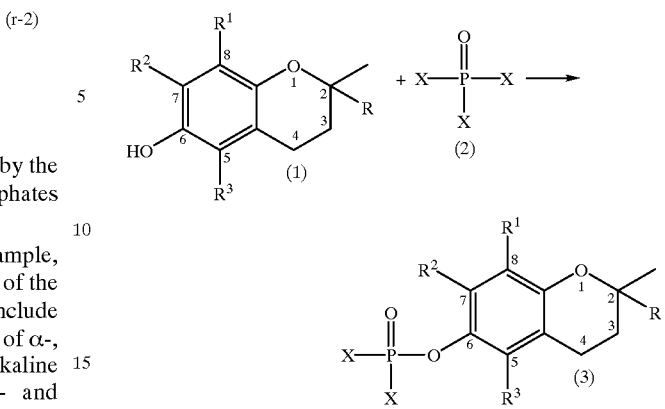

wherein $R^1$ to $R^3$ and R are as defined above, and X represents a halogen atom.

<Tocopherol>

The tocopherol is, for example, represented by the above formula (1), and specific examples thereof include α-tocopherol, β-tocopherol, γ-tocopherol and δ-tocopherol and α-, β-, γ- and δ-tocotrienols. Of these, α-tocopherol is preferably employed.

When R is $C_{16}H_{27}$, it can be represented by, for example, the above formula (r-1). On the other hand, when R is $C_{16}H_{27}$, it can be represented by, for example, the formula (r-2). Not only synthetic tocopherols but also natural tocopherols (optically active) are known. In the present invention, any of d-, l- and dl-isomers can be used.

<Oxyphosphorus Trihalide>

The oxyphosphorus trihalide (2) is not particularly limited, and the halogen atom X may be any of chlorine, bromine, fluorine and iodine. For example, oxyphosphorus trichloride can be used.

This oxyphosphorus trihalide (2) is preferably used in an amount of 1 to 5 mol equivalents, still preferably, 1 to 1.3 mol equivalents per mol of the tocopherol.

A solvent can be used in the above reaction. Examples of suitable solvents include organic nonreactive solvents such as benzene, toluene, diethyl ether, isopropyl ether and methyl tert-butyl ether.

The reaction of the tocopherol (1) with the oxyphosphorus trihalide (2) is generally conducted at −20 to 50° C., preferably, 0 to 30° C.

A base such as pyridine, triethylamine, sodium carbonate or potassium carbonate may be added as a deacidation agent in order to trap (capture, neutralize) a hydrogen halide generated by this reaction. The base can be added to the reaction system in an amount of, preferably, 1 to 5 mol equivalents and, still preferably, 1 to 2 mol equivalents per mol of the tocopherol.

As mentioned above, the oxyphosphorus dihalide compound of tocopherol, for example, represented by the above formula (3) can be obtained by reacting the tocopherol with the oxyphosphorus trihalide, preferably, under the above conditions.

In the present invention, the tocopheryl phosphate and/or salt thereof (tocopheryl phosphates) can be obtained by hydrolyzing this oxyphosphorus dihalide compound of tocopherol (3) in an acid or basic aqueous solution. In this hydrolysis, the P,P'-bistocopheryl diphoshate and/or salt thereof (P,P'-bistocopheryl diphoshates) are formed as a by-product.

First, the hydrolysis of the oxyphosphorus dihalide compound of tocopherol (3) in basic condition (formula (4)

represents a base or water, this applies hereinafter) as shown in, for example, the following formula will be described.
<Production of Highly Purified Tocopheryl Phosphate by Hydrolysis of Oxyphosphorus Dihalide Compound of Tocopherol in Basic Condition Followed by Acidic Condition>

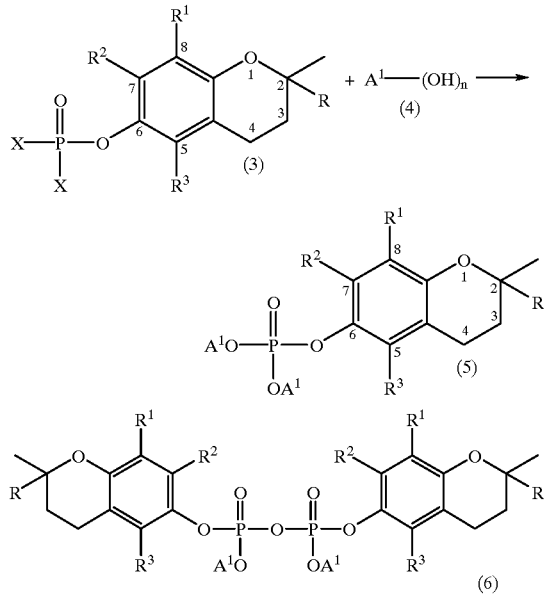

wherein, as in the above definition, each of $R^1$ to $R^3$ independently represents a methyl group or a hydrogen atom and R represents $C_{16}H_{33}$ or $C_{16}H_{27}$ and wherein $A^1$ represents a hydrogen atom, an alkali metal, an alkaline earth metal or ammonium, X represents a halogen atom and n is the number corresponding to the valence of $A^1$, provided that the formulae (5) and (6) show structures obtained when the valence of $A^1$ is 1.

In the present invention, the phosphorus-halogen bond (P—X) of the oxyphosphorus dihalide compound of tocopherol represented by the above formula (3) is hydrolyzed by, for example, the compound of the formula (4).

The base is not particularly limited and is, for example, any of hydroxides of alkali metals, alkaline earth metals and ammonium represented by the above formula $A^1$—(OH)n (4). Suitable examples thereof are sodium and potassium hydroxides.

When the base is used in the form of an aqueous solution, the base concentration ranges from 0.5 to 10 N, preferably, from 1 to 3 N. The base is used in an amount equivalent to 1 to 7 mol equivalents, preferably, 2 to 4 mol equivalents per mol of the employed tocopherol. A solvent is generally used in this reaction, which can be the same as used in the above reaction of the tocopherol with the oxyphosphorus trihalide. The hydrolysis reaction is generally conducted at 0 to 50° C., preferably, 15 to 35° C. for 30 min to 10 hr, preferably, 1 to 5 hr.

Not only is tocopheryl phosphates of the above formula (5), namely, the tocopheryl phosphate represented by the below shown formula [I] and/or salt thereof produced but also, for example, the P,P'-bistocopheryl diphoshates of the above formula (6), namely, the P,P'-bistocopheryl diphosphate represented by the below shown formula [II] and/or salt thereof is formed as a by-product by the above hydrolysis of the phosphorus-halogen bond (P—X) of the oxyphosphorus dihalide compound of tocopherol (3) with the use of the base (for example, the compound of the formula (4)).

Tocopheryl Phosphate:

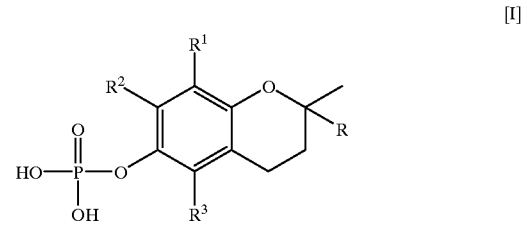

wherein $R^1$ to $R^3$ and R are as defined above. P,P'-bistocopheryl diphoshate:

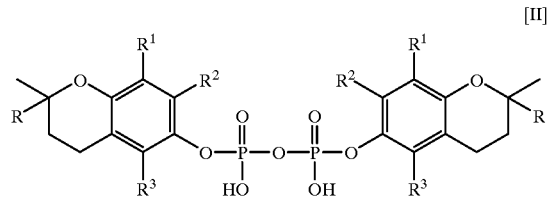

wherein $R^1$ to $R^3$ and R are as defined above.

When, for example, the tocopheryl phosphates of the above formula (5) including the compound of the above formula [I] and the P,P'-bistocopheryl diphoshates of the above formula (6) including the compound of the above formula [II] are dispersed in water at neutrality (e.g., 5 to 9 in pH), it is difficult to dissolve the P,P'-bistocopheryl diphoshates of the above formula (6) including the compound of the above formula [II], which form precipitates.

However, when the mixture of the tocopheryl phosphates represented by the formula (5) and the P,P'-bistocopheryl diphoshates represented by the formula (6) is caused to undergo a hydrolytic reaction in acid condition according to the formula:

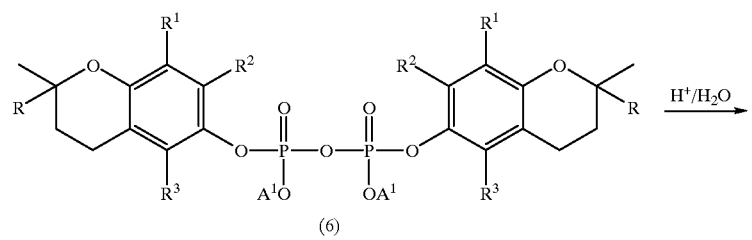

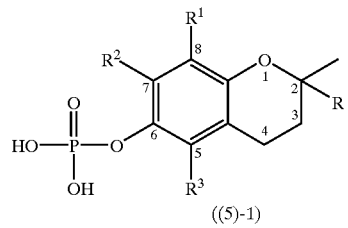

((5)-1)

wherein $R^1$ to $R^3$, R and $A^1$ are as defined above, there can be obtained only the tocopheryl phosphate of the formula (5)-1 (formula [I]).

That is, when the reaction mixture containing the tocopheryl phosphates (5) as a monomer and the secondarily formed P,P'-bistocopheryl diphoshates (6) as a dimer is caused to undergo a hydrolytic treatment in acid condition, the P,P'-bistocopheryl diphoshate of the above formula (6) and/or salt thereof (P,P'-bistocopheryl diphoshates) contained in the reaction mixture is hydrolyzed in acid condition, so that the P,P'-bistocopheryl diphoshates are converted to the tocopheryl phosphate (monomer) represented by the formula (5)-1. The tocopheryl phosphates (5) are stable during the hydrolysis of the P,P'-bistocopheryl diphoshates.

The acid for use in the above hydrolysis of the P,P'-bistocopheryl diphoshates is not particularly limited. It is, for example, sulfuric acid, hydrochloric acid or phosphoric acid. Sulfuric acid or phosphoric acid can preferably be employed.

The above acid can be diluted with water before use. Although the acid concentration of the acid aqueous solution is not particularly limited, greater dilutions are preferred from the viewpoint of convenience in the subsequent purification step. It is preferred that the acid concentration of the acid aqueous solution range from 0.5 to 1.1 N. In this reaction, a solvent can be used. Examples of suitable solvents include organic solvents such as benzene, toluene, diethyl ether, isopropyl ether, methyl tert-butyl ether and n-propyl alcohol. This reaction is generally conducted at 50° C. to a temperature at which the reaction mixture is heated and refluxed, preferably, 70 to 110° C. for 30 min to 3 hr, preferably, 1 to 2 hr.

Furthermore, with respect to the hydrolysis of the compounds (5) and (6) using the above acid, it is known that, generally, the phosphoric ester bond (P—O) is relatively easily hydrolyzed and cleaved. For example, it has been confirmed by the inventors that, when the tocopheryl phosphate of the following formula (a-1) is heated in acid condition, the reaction of the following formula occurs so that the tocopherol (a-2) and the phosphate group are very rapidly cleaved at mark "h" portion by hydrolysis to thereby form the tocopherol (a-2) and glycerophosphoric acid (a-3):

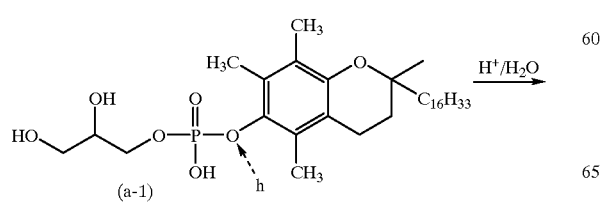
(a-1)

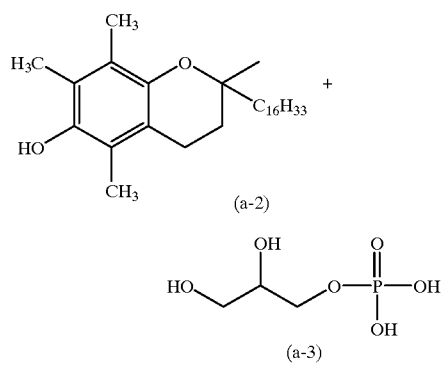

(a-2)

(a-3)

It has been found, however, by the inventors that, even when heated at 100° C. in acid condition in the same manner as above, the hydrolysis of the tocopherol-phosphate bond (C—O—P) does not proceed at all in the tocopheryl phosphate containing no glycerol moiety as in the present invention and meanwhile the P,P'-bistocopheryl diphoshates of the formula (6) are hydrolyzed so that the desired tocopheryl phosphate can be obtained. <Production of highly purified tocopheryl phosphate by hydrolysis of oxyphosphorus dihalide compound of tocopherol in acidic condition>

The hydrolysis of the above oxyphosphorus dihalide compound of tocopherol (3) with the use of an acid (including an acid aqueous solution, this applies hereinbelow) according to, for example, the following formula will be described below:

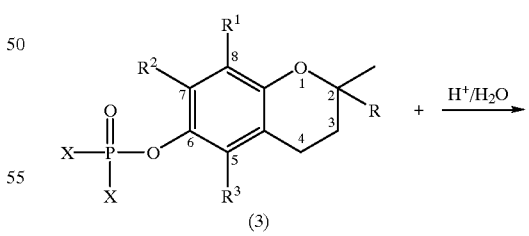
(3)

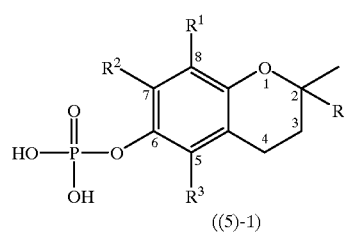
((5)-1)

-continued

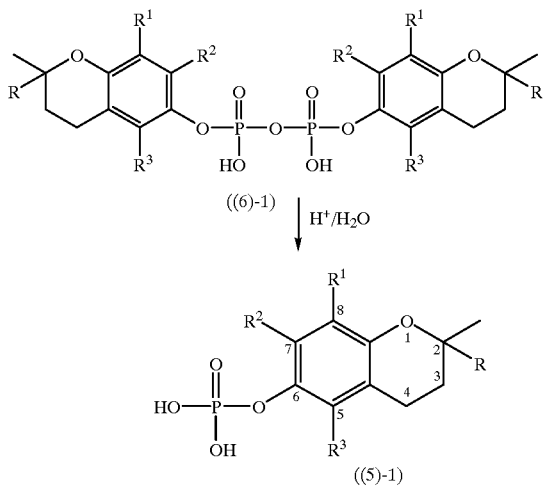

wherein $R^1$ to $R^3$ and R are as defined above.

The above hydrolysis of the tocopheryl-containing dihalide compound oxyphosphorus (3) in acid condition splits the phosphorus-halogen bond (P—X) of this compound (3) by the action of water, so that not only is the tocopheryl phosphate of the above formula (5)-1 formed but also the P,P'-bistocopheryl diphoshate of the above formula (6)-1 is formed as a by-product.

In this acid condition, however, further heating hydrolyzes the P—O—P bond of the P,P'-bistocopheryl diphoshate of the above formula (6)-1. As a result, only the tocopheryl phosphate of the above formula (5)-1 is formed by the reaction in acid condition.

That is, reacting the tocopherol (1) with the oxyphosphorus trihalide (2) and hydrolyzing the reaction mixture in acid condition enables production of the tocopheryl phosphate (5)-1 in higher efficiency with less steps than in the above process comprising hydrolyzing the compound (3) with a base and conducting further hydrolysis in acid condition.

The acid for use in the above reaction is not particularly limited. It is, for example, sulfuric acid, hydrochloric acid or phosphoric acid.

The above acid can be diluted with water before use. The acid concentration of the acid aqueous solution ranges from 0.5 to 10 N, preferably, from 3 to 9 N. The acid is used in an amount of 0.5 to 5 mol equivalents, preferably, 1 to 3 mol equivalents per mol of the base used as the deacidation agent Further, in this reaction, a solvent can be used. The same solvents that were used in the reaction of the tocopherol with the oxyphosphorus trihalide can be used. This reaction is generally conducted at 50° C. to a temperature at which the reaction mixture is heated and refluxed, preferably, 70 to 110° C. for 1 to 5 hr, preferably, 2 to 4 hr.

In the present invention, the thus obtained tocopheryl phosphate may optionally be neutralized or rendered basic with the use of the above basic aqueous solution.

Although the highly purified tocopheryl phosphate of the formula [I] (formula (5)-1) and/or salt thereof which has been produced by the above process exhibits low toxicity and, as it is, can be used as a cosmetic ingredient, the tocopheryl phosphate of the formula [I] may optionally be reacted with a base in an organic solvent or a mixed solvent of water and an organic solvent so that the tocopheryl phosphate is converted to a pharmacologically acceptable salt of tocopheryl phosphate.

The tocopheryl phosphate may be in the form of a salt, for example, an inorganic salt such as a sodium, a potassium, a magnesium or an aluminum salt or an amine salt such as a hexylamine salt. Alkali metal salts such as sodium and potassium salts having high water solubility are preferred.

In the formation of a salt of tocopheryl phosphate, the tocopheryl phosphate is generally reacted in a solvent with, for example, an alkali metal hydroxide capable of forming the above salt.

In this reaction, the tocopheryl phosphate represented by the formula [I] is preferably dissolved in an organic solvent. Examples of suitable organic solvents include alcohols such as methanol, ethanol, 1-propanol and 2-propanol. The solvent is preferably used in an amount of ¼ to 5 times the weight of the tocopheryl phosphate.

In the present invention, the salt forming reaction is performed by dropping a solution obtained by dissolving 0.5 to 1.5 mol equivalents, preferably, 0.9 to 1.1 mol equivalents, per mol of the tocopheryl phosphate, of an alkali metal hydroxide such sodium hydroxide or potassium hydroxide in water or an organic solvent, preferably, an alcohol such as methanol or ethanol into the thus prepared solution of tocopheryl phosphate.

It is preferred that the concentration of alkali metal hydroxide in the dropped solution is low from the viewpoint that the decomposition of the tocopheryl phosphate can be prevented. The concentration is especially preferred to range from 1 to 5 N. In the above dropping of the alkali metal solution, the reaction system is preferred to be set at 0 to 50° C., especially, 10 to 30° C.

The thus synthesized highly purified tocopheryl phosphate of the formula [I] and/or alkali metal salt thereof (highly purified tocopheryl phosphates) scarcely contains or does not contain at all the P,P'-bistocopheryl diphoshate [II], so that the following clear solution is provided.

That is, a clear aqueous solution is provided by causing the tocopheryl phosphate (tocopheryl phosphates) to be contained in an amount of 3% by weight, adding water so that the pH value of the solution becomes 8.5 and, optionally, regulating the pH value with the addition of sodium hydroxide or phosphoric acid.

The tocopheryl phosphates containing material obtained by the above process is highly pure and scarcely contains or does not contain at all the P,P'-bistocopheryl diphoshates. The content of P,P'-bistocopheryl diphoshates is only up to 3% by weight (namely, 97 to 100% by weight of tocopheryl phosphate (i)), preferably, only up to 0.5% by weight (namely, 99.5 to 100% by weight of tocopheryl phosphate (i)) per 100% by weight of the total of tocopheryl phosphates (i) and P,P'-bistocopheryl diphoshates (ii).

The cosmetic of the present invention will be described in detail below.

Cosmetic

The cosmetic of the present invention contains the above tocopheryl phosphate and/or salt thereof (tocopheryl phosphates).

When the cosmetic is a liquid cosmetic whose pH value ranges from 5 to 9, especially, a transparent toilet water of the aqueous solution type, in the present invention, the tocopheryl phosphate is preferred to be in the form of a sodium or potassium salt having high water solubility. When the salt of tocopheryl phosphate is added to cosmetics other than the toilet water, any salt can be employed as long as its impurity content is low and its toxicity is physiologically acceptable in the use as a cosmetic. The salt can be an inorganic salt such as a magnesium salt or an aluminum salt or an amine salt such as a hexylamine salt.

The content of impurities of P,P'-bistocopheryl diphoshates (ii) (hereinafter may be referred to as "bis derivative")

in the highly purified tocopheryl phosphates of the present invention is only up to 3% by weight and the content (purity) of tocopheryl phosphates (i) is at least 97% by weight per 100% by weight of the total of tocopheryl phosphates (i) and P,P'-bistocopheryl diphoshates (ii). Preferably, the content of the bis derivative is up to 2% by weight while the purity of the above component (content of the component (i)) is at least 98% by weight. Still preferably, the content of the bis derivative is up to 0.5% by weight while the purity of the above component ranges from 99.5 to 100% by weight.

In the above case, the bis derivative content and purity are measured by using a high-performance liquid chromatography of a column packed with a gel of a polymethacrylate having, bonded thereto, octadecyl groups. The analytical conditions are such that the column temperature is 38 to 42° C. and the analysis is conducted with the use of a 100/0.9 to 100/1.1 mixture of methanol/water containing 0.04 to 0.06 M sodium acetate as an eluate and with the use of a spectrophotometer for ultraviolet and visible region as a detector. The detection wavelength is 287 nm.

The highly purified tocopheryl phosphates for use in the present invention, formulated into a 3% by weight aqueous solution with a pH value of 5 to 9, preferably, 8.5, are clear or substantially clear when measured in accordance with the below described standards. The water solubility thereof remains high irrespective of the passage of time and the formulation thereof into a cosmetic does not cause precipitation or clouding.

Herein, the simple expression "%" sometimes used means "% by weight" unless it is in conflict with the context.

The highly purified tocopheryl phosphate and/or water soluble salt such as alkali metal or aluminum salt thereof according to the present invention has a water solubility which is excellent as markedly different from those of conventional items. Therefore, whether a material can be added to the cosmetic of the present invention can be judged with a certain level of appropriateness on the basis of solubility difference even when a high-performance liquid chromatogram is not available.

That is, if tocopheryl phosphates are dissolved in a water with a pH value of, preferably, 8.5 in a concentration of 3% by weight to thereby provide a clear solution, they can be used in the cosmetic of the present invention.

Although the added amount is not particularly limited, the tocopheryl phosphate and/or salt thereof (tocopheryl phosphates) according to the present invention is generally added to the cosmetic in an amount such that its total concentration is at least 0.0001 mol per 100 g of cosmetic in the anticipation that the effects thereof are exerted. Although no particular reports have been published with respect to toxicities of tocopheryl phosphates, it is preferred that the concentration thereof in customary cosmetic preparations do not exceed an upper limit of 50% by weight because of probable needs to be vigilant against vitamin E-related hypervitaminosis. However, this does not necessarily apply to dosage forms such as powder cosmetic which are each employed in the form of a dilution.

The cosmetic of the present invention can have any of all dosage forms available as long as the tocopheryl phosphates of the present invention can be added thereto, which include a cream, an essence, a toilet water, a milky lotion, a powder, a mousse, a manicure, a lip cream, a pack dentifrice, a throat washing, a troche, a bath medicine, a shampoo, a rinse, a hair tonic, a hair growth stimulant, a hair grower and a scalp medicine.

Conventional emulsifiers can be added in common concentrations to the cosmetic of the present invention for the purpose of dissolving ingredients other than the tocopheryl phosphates of the present invention and for the purpose of adding moisture retaining and cleaning capabilities which are fundamental objects of cosmetics.

The addition of any of L-ascorbic acid phosphates and salts thereof, such as magnesium salt of L-(ascorbic acid)-2-phosphate and sodium salt of L-(ascorbic acid)-2-phosphate, and L-ascorbic acid derivatives and salts thereof, such as L-ascorbic acid glucoside, L-ascorbic acid palmitate and L-ascorbic acid stearate, to the tocopheryl phosphates containing cosmetic of the present invention synergistically increases the radical trapping activity of each of these components, so that it is especially effective in a cosmetic as a countermeasure against, for example, aging and ultraviolet, and a hair grower, etc.

Stabilizers can be added to the cosmetic of the present invention, which are, for example, antioxidant substances. Examples of the antioxidant substances include vitamin A, vitamin B, vitamin C, vitamin E, vitamin E nicotinate, vitamin E acetate and ubiquinone and, further, vitamin derivatives and salts thereof; carotinoids such as astaxanthin; and other antioxidant substances such as cysteine, glutathione, glutathione peroxidase, SOD, citric acids, phosphoric acids, polyphenols, nucleic acids, Chinese medicines, sea weeds and inorganic substances.

Ultraviolet absorbers as other stabilizers than above such as paraamino acid, hydroxybenzophenone, benzofuran, salicylic acid, coumarin and azol ultraviolet absorbers can be added to the cosmetic of the present invention, which would prevent the decomposition of tocopheryl phosphates by ultraviolet.

Bleaching cosmetic ingredients used in common cosmetics may be added together with the above ingredients to the cosmetic of the present invention. Examples of bleaching ingredients which can be added (used) include kojic acid, placenta extract and arbutin.

Further, conventional antiinflammatory or antiphlogistic ingredients can be added to the cosmetic of the present invention, the combined use or mixing of which induces a synergistic effect with the tocopheryl phosphate to thereby promote the antiinflammatory effect.

Examples of the antiinflammatory ingredients which can be added to the cosmetic of the present invention include an antiinflammatory agent of the salicylic acid derivative type, an antiinflammatory agent of the aniline derivative type, a spasmolytic, an antiinflammatory agent of the pyrazolone derivative type, an antiinflammatory agent of the indomethacin type, an antiinflammatory agent of the mefenamic acid type, an antihistamic agent, an antiallergic agent and an antiinflammatory enzyme agent, which in no way limit the scope of the employable antiinflammatory ingredients.

Moreover, known additives as set forth in cosmetic additive specifications such as Off-standard Cosmetic Ingredient Specification 1993 supplement (Yakuji Nippo, Ltd.) can be added for common purposes to the cosmetic of the present invention.

The tocopheryl phosphate, salt thereof or a mixture thereof according to the present invention can be added to the cosmetic of the present invention in a form coated with a coating material such as a gelatin, an oil, a fat or the like or in a form clad with a microcapsule, dextrin or the like according to necessity.

The cosmetic compounded with the highly purified tocopheryl phosphates of the present invention is excellent in physical stability as compared with that of the cosmetic compounded with common tocopheryl phosphates. This is attributed to the presence of an insoluble impurity of P,P'-bistocopheryl diphoshate in the common tocopheryl phosphates, whereby the properties which are different from those of the original pure tocopheryl phosphate and/or salt thereof are exhibited.

None or, if any, only an extremely minute amount (3% by weight or below, preferably, 2% by weight or below and, still preferably, 0.5% by weight or below per 100% by weight of the total of components (i) and (ii)) of P,P'-bistocopheryl diphoshates are contained in the tocopheryl phosphate of the formula [I] and/or salt thereof (e.g., alkali metal salt) (i) added to the cosmetic of the present invention. Therefore, the tocopheryl phosphate and/or salt thereof can be dissolved in water at neutrality to thereby provide a solution, so that stable cosmetic preparations can be obtained therefrom.

The tocopheryl phosphate is one in which the tocopherol is bonded with phosphoric acid and exerts the inherent effects of the tocopherol, namely, antioxidant and blood circulation promoting effects. Further, the tocopheryl phosphate has an improved water solubility. Still further, powder of low moisture absorption is provided, the handling of which is extremely easy. The tocopheryl phosphate is free from cutaneous irritation and allergenecity and ensures dermal safety. Therefore, the tocopheryl phosphate is useful as an cosmetic ingredient.

Analysis of Tocopheryl Phosphates

Now, the method of analyzing tocopheryl phosphates according to the present invention will be described below.

In the measuring of the content of tocopheryl phosphate and/or alkali metal salt thereof [I] according to the present invention, a high-performance liquid chromatograph column packed with a gel of a poly(meth)acrylate having, bonded thereto, long-chain alkyl groups is used to thereby conduct effective analysis.

The analytical method of the present invention can be carried out with the use of, for example, an analytical instrument as shown in FIG. 1. Illustratively, an eluate 1 is fed by means of a liquid feeding pump 2 into a high-performance liquid chromatograph column 5 packed with a gel of a polymethacrylate having, bonded thereto, long-chain alkyl groups. Concurrently, an analytical sample 3 is injected through a sample injector part 4 into the eluate. Sample separation is carried out in the above column 5. The eluate from this column is fed to a spectrophotometrical detector for ultraviolet and visible region 6 by which analysis and detection are carried out. According to necessity, recording is made with the use of a recorder (not shown).

The analytical column for use in the analytical method of the present invention is preferred to be a column packed with a gel of a polymethacrylate having, bonded thereto, long-chain alkyl groups. In the gelpacked column, the above long-chain alkyl groups are preferred to be linear or branched alkyl groups each having 6 to 60 carbon atoms, especially, 8 to 28 carbon atoms. A column packed with a gel of a polymethacrylate having, bonded thereto, octadecyl groups (e.g., Shodex RS pak D18-613 and DE 413 produced by Showa Denko K.K.) is most suitable.

In the present invention, there is no particular limit on the members constituting the analytical instrument as long as the above packing material is employed. Common liquid feeding pump, sample injector, detector and recorder customarily used in high-performance liquid chromatographs can be employed.

The material, shape and size of the column to be packed with the above packing material are not particularly limited. For example, a stainless steel column can suitably be used.

Although the eluate is not particularly limited as long as it is capable of separating tocopheryl phosphates from impurities, it is preferred that the eluate be composed of methanol (MeOH) and water (containing sodium acetate). In the present invention, the volume ratio of MeOH to $H_2O$ is preferred to be in the range of 100/0.9 to 100/1.1, especially, 100/1 (containing 0.05 mol of $CH_3COONa$ per liter of the total of MeOH and water) from the viewpoint that the separation performance is excellent.

The analytical method of the present invention enables measuring the purity of tocopheryl phosphate and/or salt thereof (e.g., alkali metal salt) (in other words, content of impurities) in a sample such as cosmetic sample more simply and with higher precision (more accurately) than in the conventional analytical method.

Therefore, the measuring of the quantity of tocopheryl phosphate in cosmetic preparation can be facilitated.

EFFECT OF THE INVENTION

None or only an extremely minute amount of P,P'-bistocopheryl diphoshates are contained in the highly purified tocopheryl phosphates of the present invention. The highly purified tocopheryl phosphates exhibit antioxidant and blood circulation promoting effects and have markedly enhanced water solubility as compared with those of the conventional tocopheryl phosphates containing materials.

The highly purified tocopheryl phosphates are powdery so that the handling thereof is extremely easy, are free from cutaneous irritation and allergenecity and ensure dermal safety. Therefore, the highly purified tocopheryl phosphates are useful as cosmetic ingredients.

The cosmetic in which the above highly purified tocopheryl phosphates are contained has the above characteristics.

Even if the cosmetic of the present invention is aqueous and is consumed after the passage of a prolonged period of time, the contained tocopheryl phosphates do not form any insoluble precipitates in the cosmetic of the present invention. Thus, the cosmetic of the present invention is excellent in the time (storage) stability of quality.

The conventional analytical methods have been unable to satisfactorily analyze the cause of precipitation occurring at the storage of a tocopheryl phosphates containing cosmetic for a prolonged period of time.

In contrast, the analytical method for tocopheryl phosphates having been found by the inventors has identified by the use of a high-performance liquid chromatography using a column packed with a gel of a poly(meth)acrylate having, bonded thereto, long-chain alkyl groups (preferably, octadecyl groups) that the above cause would be the mixing of impurities of P,P'-bistocopheryl diphoshates. The content of such impurities can be rendered substantially zero or can be suppressed to an extremely low level by producing the tocopheryl phosphates according to the above process of the present invention. The use of the highly purified tocopheryl phosphates of the present invention which contain none or only an extremely minute amount of such impurities in a cosmetic can provide the cosmetic which is excellent in stability, especially, time stability and which is free from precipitation of insoluble matter.

In the analytical method of the present invention, a high-performance liquid chromatography column packed with a gel of a polymethacrylate having, bonded thereto, long-chain alkyl groups (preferably, octadecyl groups) is used to thereby measure the contents of tocopheryl phosphates and P,P'-bistocopheryl diphoshates more accurately and more simply than in the conventional analytical methods.

EXAMPLE

The present invention will be further illustrated below with reference to the following Examples, which in no way limit the scope of the invention.

The term "%" used hereinafter means "% by weight" and, in each preparation, the respective percents of all the ingredients thereof total 100% by weight unless this is in conflict with the context.

Example A-1

25.0 g (0.05 mol) of dl-α-tocopherol was dissolved in 75 ml of toluene containing 9.3 g of pyridine.

9.8 g (0.064 mol) of oxyphosphorus trichloride was dropped into this solution at room temperature (about 15° C.) to 50° C. under agitation.

After the completion of the dropping, a further reaction was carried out at room temperature for 3 hr. Subsequently, 100 ml of a 10% aqueous solution of sulfuric acid was added to thereby dissolve any precipitated salt. The mixture was separated into an organic layer and a water layer by a separatory funnel.

100 ml of a 10% aqueous solution of sulfuric acid was added to the separated organic layer and the mixture was heated under reflux for 4 hr to thereby effect a reaction.

Thereafter, 5 ml of methanol was added to the reaction mixture, and an organic layer was separated. The organic layer was washed with 100 ml of a 5% aqueous solution of sulfuric acid, concentrated and dried. 100 ml of 2-propanol was added to the obtained dried concentrate.

25 ml of methanol in which 2.4 g of sodium hydroxide was dissolved was dropped into the mixture and reacted for 1 hr with the temperature kept unchanged. Formed precipitate was separated, dissolved in 1 lit. of methanol and concentrated to 150 ml. Then, 200 ml of acetone was dropped into the concentrate to thereby form white precipitate. The precipitate was washed with acetone and dried in vacuum, thereby obtaining 18.2 g of white powder of highly purified sodium salt of dl-α-tocopheryl phosphate.

$^{31}$P-NMR (CD$_3$OD, δ value, unit: ppm, reference: 85% phosphoric acid)
2.9
Infrared absorption spectrum (FT-IR, KBr, cm$^{-1}$)
1030
1111
1169
1250
2500 to 3200
Elementary analysis

|   | Calculated (%, note 1) | Measured (%) |
|---|---|---|
| C: | 65.39 | 65.80 |
| H: | 9.46 | 9.13 |

Note 1:
calculated assuming the formula of C$_{29}$H$_{50}$O$_5$PNa.

Example A-2

25.0 g (0.058 mol) of dl-α-tocopherol was dissolved in 75 ml of toluene containing 9.3 g of pyridine and cooled to 0° C. on an ice bath.

9.8 g (0.064 mol) of oxyphosphorus trichloride was dropped into the cooled solution over a period of 5 min under agitation.

After the completion of the dropping, the ice bath was removed and a further reaction was carried out for 3 hr. Subsequently, 50 ml of a 6N aqueous solution of sulfuric acid was added and heated under reflux for 3 hr. The mixture was separated into an organic layer and a water layer by a separatory funnel. The organic layer was washed with a 1N aqueous solution of hydrochloric acid and dried over anhydrous sodium sulfate. The organic layer was concentrated and dried by means of an evaporator. 100 ml of 1-propanol was added to the obtained dried concentrate.

25 ml of methanol in which 2.40 g of sodium hydroxide was dissolved was dropped into the mixture, heated to 35 to 40° C. and reacted for 1 hr at that temperature. Formed precipitate was separated, dissolved in 1 lit. of methanol and concentrated to 150 ml. Then, 20 ml of acetone was dropped into the concentrate to thereby form white precipitate. The precipitate was washed with acetone and dried in vacuum, thereby obtaining 18.9 g of white powder.

The thus obtained highly purified sodium salt of dl-α-tocopheryl phosphate was analyzed in the same manner as in Example A-1. All the $^{31}$P-NMR chemical shift and peak positions of infrared absorption spectrum agreed with those described in Example A-1, and the elementary analysis values also agreed therewith within limits of error.

Example A-3

25.0 g (0.05 mol) of dl-α-tocopherol was dissolved in 75 ml of methyl tert-butyl ether containing 9.3 g of pyridine and cooled to 0° C. on an ice bath.

9.8 g (0.064 mol) of oxyphosphorus trichloride was dropped into the cooled reaction system over a period of 5 min under agitation.

After the completion of the dropping, the ice bath was removed and a further reaction was carried out for 3 hr. Subsequently, 95 ml of a 2N aqueous solution of sodium hydroxide was added and agitated for 10 min. Further, 100 ml of a 10% aqueous solution of sulfuric acid was added and the mixture was separated into an organic layer and a water layer by a separatory funnel.

The separated organic layer was washed with a 1N aqueous solution of hydrochloric acid and dried over anhydrous sodium sulfate. The organic layer was concentrated and dried by means of an evaporator. 100 ml of toluene and 100 ml of a 1N aqueous solution of sulfuric acid were added to the obtained dried concentrate and heated under reflux for 2 hr to thereby effect a reaction.

The organic layer was separated, concentrated and dried. The obtained dried concentrate was recrystallized from 150 ml of hexane, thereby obtaining 19.8 g of dl-α-tocopheryl phosphate.

Example A-4

20 μl of a solution obtained by dissolving 10 mg of (±)-DL-tocopheryl phosphate (produced by Sigma) in an eluate was injected in an analytical instrument including a column packed with a gel of a polymethacrylate having, bonded thereto, octadecyl groups (Shodex RS pak D18-613 of 6 mm in diameter and 150 mm in length) and a spectrophotometrical detector for ultraviolet and visible region as shown in FIG. 1, and an analysis was conducted. Thus, a chromatogram of FIG. 2 was obtained.

Figure 2:
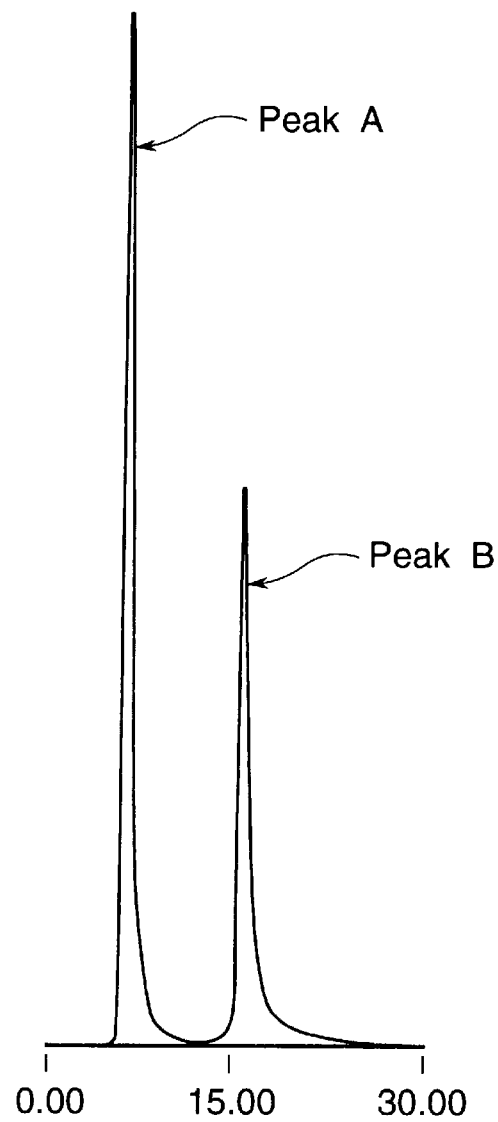
FIG. 2 is a chromatogram showing the result of Analytical Example 1.

It is apparent from the results of $^{31}$P-NMR that, in FIG. 2, the peak A corresponds to tocopheryl phosphate and the peak B corresponds to P,P'-bistocopheryl diphoshate. The analysis was conducted under the following conditions:

Eluate: MeOH/H$_2$O of 100/1 in volume ratio (containing 0.05 mol of CH$_3$COONa per liter of the total of MeOH and H2O), Elution rate: 0.5 ml/min, Spectrophotometer for ultraviolet and visible region: 875-UV manufactured by Japan Spectroscopic Co., Ltd., Detection wavelength: 287 nm, and Column temperature: 40° C.

Example A-5

Figure 3:
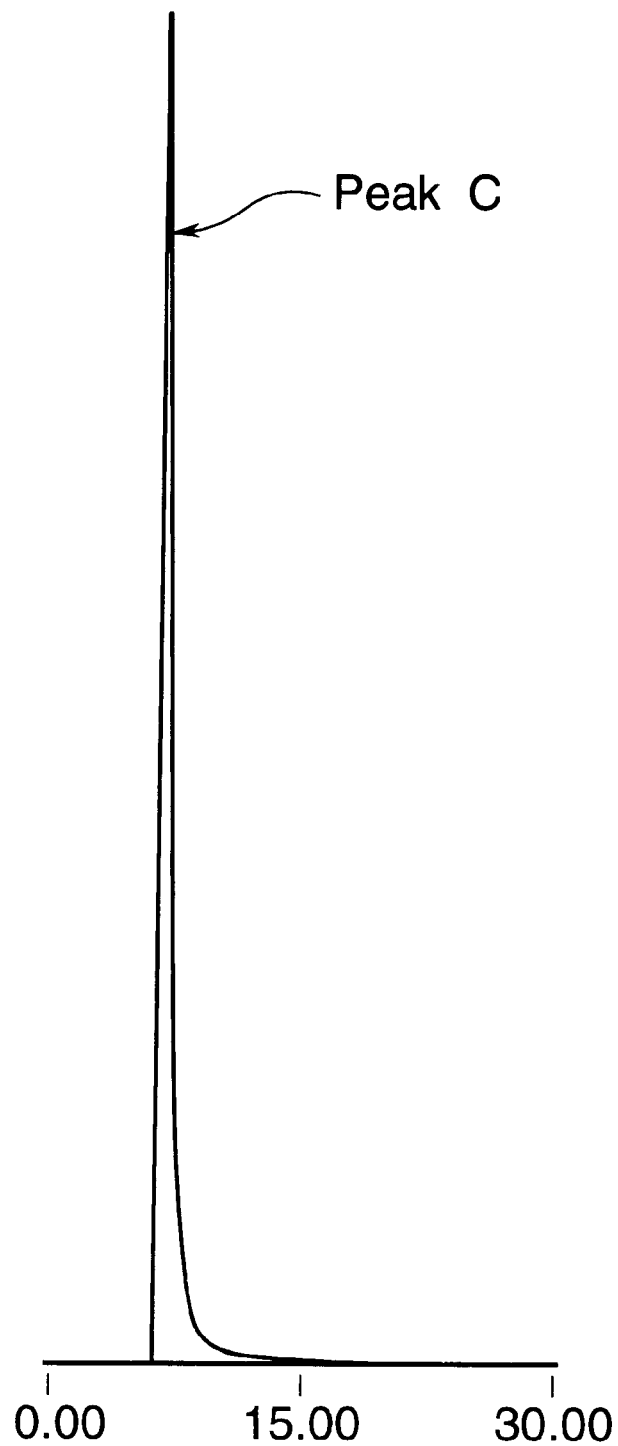
FIG. 3 is a chromatogram showing the result of Analytical Example 2.

The highly purified sodium salt of dl-α-tocopheryl phosphate obtained in Example A-1 was analyzed under the same conditions as in Example 3, thereby obtaining a chromatogram of FIG. 3. The peak C had the same retention time as that of the peak A in Example 3. Therefore, it is apparent that the compound giving the peak C, namely, the white powder obtained by the operation described in Example A-1 is a tocopheryl phosphate. The amount of P,P'-bistocopheryl diphoshate was below the detection limit.

Example A-6

3.0 g of the highly purified sodium salt of dl-α-tocopheryl phosphate obtained in Example A-1 was dissolved in 87 ml of water at room temperature (25° C.), and 1N hydrochloric acid was gradually dropped thereinto to regulate the pH value of the aqueous solution. Thus, an aqueous solution with a pH value of 8.5 was obtained. In this process, pH meter (pH meter D-12 manufactured by Horiba Seisakusho Co., Ltd.) was used.

Water was added to the aqueous solution so that the total weight thereof was 100 g. The aqueous solution was clear or substantially clear.

3.0 g of the highly purified dl-α-tocopheryl phosphate obtained in Example A-3 was suspended in 77 ml of water at room temperature (25° C.), and 12 ml of a 1N aqueous solution of sodium hydroxide was gradually dropped to thereby dissolve the dl-α-tocopheryl phosphate. Subsequently, a 1N aqueous solution of hydrochloric acid was gradually dropped thereinto to regulate the pH value of the aqueous solution. Thus, an aqueous solution with a pH value of 8.5 was obtained. In this process, pH meter (pH meter D-12 manufactured by Horiba Seisakusho Co., Ltd.).

Water was added to the aqueous solution so that the total weight thereof was 100 g. The aqueous solution was clear or substantially clear.

Criteria for Evaluation "Clear or Substantially Clear"

Herein, the evaluation "clear or substantially clear" is made on the basis of the criteria set forth on pages 1312–1313, general rule, commentary II, 2nd edition of "Japanese Standards of Cosmetic Ingredients" edited by Society of Japanese Pharmacopoeia and published by Yakuji Nippo, Ltd. in 1984.

That is, the "clear" is defined as the state of being not over a turbidity exhibited when water is added to 0.2 ml of the below described turbidity standard solution so that the total volume becomes 20 ml and 1 ml of diluted nitric acid (diluted by adding water to 1 vol. of nitric acid so that the total volume becomes 3 vol.; described as "1→3"; this applies hereinbelow), 0.2 ml of a dextrin solution (water added to 1 g of dextrin so that the total volume becomes 50 ml; described as "1→50"; this applies hereinbelow) and 1 ml of a silver nitrate reagent solution are added thereto and allowed to stand still for 15 min, provided that mixing of foreign matters such as floats is substantially not observed.

The "substantially clear" is defined as the state of being not over a turbidity exhibited when water is added to 0.5 ml of the turbidity standard solution so that the total volume becomes 20 ml and 1 ml of diluted nitric acid (1→3), 0.2 ml of a dextrin solution (1→50) and 1 ml of a silver nitrate reagent solution are added thereto and allowed to stand still for 15 min, provided that mixing of foreign matters such as floats is substantially not observed.

The above turbidity standard solution is prepared by adding water to 14.1 ml of 0.1 N hydrochloric acid so that the total volume accurately becomes 50 ml, taking 10.0 ml therefrom and adding water thereto so that the total volume becomes 1000 ml.

Cosmetic

Although the cosmetic of the present invention will be illustrated in greater detail below, the formulations of tocopheryl phosphate and/or salt thereof which can be employed in the cosmetic of the present invention are in no way limited by the following examples.

Table 1 lists the abbreviations for the ingredients employed in the following examples (cosmetics).

TABLE 1

| Description of ingredient | Abbreviation |
| --- | --- |
| dl-α-tocopheryl phosphate | VEP-1 |
| sodium salt of dl-α-tocopheryl phosphate | VEP-2 |
| d-α-tocopheryl phosphate | VEP-3 |
| sodium salt of d-α-tocopheryl phosphate | VEP-4 |
| potassium salt of dl-α-tocopheryl phosphate | VEP-5 |
| magnesium salt of dl-α-tocopheryl phosphate | VEP-6 |

Among the tocopheryl phosphates listed in Table 1, dl-α-tocopheryl phosphate (VEP-1) was prepared by the above process of Example A-3 and sodium salt of dl-α-tocopheryl phosphate (VEP-2) was prepared by the above process of Example A-1. The other tocopheryl phosphates of Table 1 were each produced by the process which was similar to one of the processes of Examples A-1 to A-3.

Example B-1

A toilet water was produced by the customary procedure in accordance with the following recipe:

| | |
| --- | --- |
| ethyl alcohol | 39.6% |
| 1,3-butylene glycol | 9.5% |
| castor oil | 4.9% |
| VEP-2 | 1.0% |
| magnesium salt of (ascorbic acid)-2-phosphate | 1.0% |
| sodium salt of (ascorbic acid)-2-phosphate | 1.0% |
| methyl paraben | 0.2% |
| purified water | balance |

Example B-2

A milky lotion was produced by the customary procedure in accordance with the following recipe:

| | |
| --- | --- |
| avocado oil | 11.0% |
| behenyl alcohol | 0.6% |
| stearic acid | 0.4% |
| glycerol fatty acid ester | 0.9% |
| polyoxyethylene sorbitan fatty acid ester | 1.1% |
| polyoxyethylene alkyl ether | 0.4% |

| | |
|---|---|
| VEP-2 | 1.0% |
| magnesium salt of (ascorbic acid)-2-phosphate | 1.0% |
| sodium salt of (ascorbic acid)-2-phosphate | 1.0% |
| 1,3-butylene glycol | 10.1% |
| methyl paraben | 0.2% |
| perfume | 0.4% |
| purified water | balance |

Example B-3

A cream was produced by the customary procedure in accordance with the following recipe:

| | |
|---|---|
| squalane | 11.1% |
| stearic acid | 7.8% |
| stearyl alcohol | 6.0% |
| bees wax | 1.9% |
| propylene glycol monostearate | 3.1% |
| polyoxyethylene cetyl ether | 1.1% |
| VEP-2 | 1.0% |
| magnesium salt of (ascorbic acid)-2-phosphate | 1.0% |
| sodium salt of (ascorbic acid)-2-phosphate | 1.0% |
| 1,3-butylene glycol | 11.9% |
| methyl paraben | 0.2% |
| perfume | 0.4% |
| purified water | balance |

Example B-4

A pack was produced by the customary procedure in accordance with the following recipe:

| | |
|---|---|
| polyvinyl alcohol | 14.5% |
| sodium salt of carboxymethylcellulose | 4.8% |
| 1,3-butylene glycol | 2.9% |
| VEP-2 | 1.0% |
| magnesium salt of (ascorbic acid)-2-phosphate | 1.0% |
| sodium salt of (ascorbic acid)-2-phosphate | 1.0% |
| ethyl alcohol | 10.0% |
| methyl paraben | 0.1% |
| purified water | balance |

Example B-5

A lip color was produced by the customary procedure in accordance with the following recipe:

| | |
|---|---|
| castor oil | 45.3% |
| hexadecyl alcohol | 25.2% |
| lanolin | 3.9% |
| bees wax | 4.8% |
| ozokerite | 3.4% |
| candelilla wax | 6.2% |
| carnauba wax | 2.1% |
| methyl paraben | 0.1% |
| VEP-2 | 1.0% |
| magnesium salt of (ascorbic acid)-2-phosphate | 1.0% |
| sodium salt of (ascorbic acid)-2-phosphate | 1.0% |
| titanium oxide | 2.1% |
| red pigment | 4.8% |
| perfume | 0.1% |
| water | balance |

Example B-6

A foundation was produced by the customary procedure in accordance with the following recipe:

| | |
|---|---|
| liquid paraffin | 23.5% |
| isopropyl palmitate | 14.3% |
| lanolin alcohol | 1.8% |
| lanolin acetate | 2.9% |
| microcrystalline wax | 6.5% |
| ozokerite | 7.7% |
| candelilla wax | 0.4% |
| methyl paraben | 0.1% |
| VEP-2 | 1.0% |
| magnesium salt of (ascorbic acid)-2-phosphate | 1.0% |
| sodium salt of (ascorbic acid)-2-phosphate | 1.0% |
| titanium oxide | 14.5% |
| kaolin | 13.9% |
| talc | 5.7% |
| color pigment | 3.9% |
| perfume | 0.5% |
| water | balance |

Example B-7

A tooth paste was produced by the customary procedure in accordance with the following recipe:

| | |
|---|---|
| secondary calcium phosphate dihydrate | 45.5% |
| sodium salt of carboxymethylcellulose | 0.5% |
| carrageenan | 0.5% |
| glycerol | 9.8% |
| sorbitol | 9.7% |
| saccharin sodium | 0.1% |
| sodium lauryl sulfate | 2.3% |
| sodium chloride | 2.1% |
| α-tocopherol | 0.4% |
| VEP-2 | 1.0% |
| magnesium salt of (ascorbic acid)-2-phosphate | 1.0% |
| sodium salt of (ascorbic acid)-2-phosphate | 1.0% |
| antiseptic | 0.1% |
| perfume | 0.5% |
| purified water | balance |

Example B-8

A gargle was produced by the customary procedure in accordance with the following recipe:

| | |
|---|---|
| ethyl alcohol | 34.6% |
| glycerol | 14.5% |
| α-tocopherol | 0.4% |
| VEP-2 | 1.0% |
| magnesium salt of (ascorbic acid)-2-phosphate | 1.0% |
| sodium salt of (ascorbic acid)-2-phosphate | 1.0% |
| perfume | 0.1% |
| purified water | balance |

Example B-9

A hair grower was produced by the customary procedure in accordance with the following recipe:

| | |
|---|---|
| ethyl alcohol | 60.0% |
| castor oil | 4.3% |
| resorcinol | 0.7% |
| methyl paraben | 0.1% |
| capsicum tincture | 0.4% |
| α-tocopherol | 0.5% |
| VEP-2 | 1.5% |
| magnesium salt of (ascorbic acid)-2-phosphate | 1.0% |
| sodium salt of (ascorbic acid)-2-phosphate | 1.0% |
| purified water | balance |

Example B-10

A shampoo was produced by the customary procedure in accordance with the following recipe:

| | |
|---|---|
| lauryl acid triethanolamine | 15.0% |
| lauric acid diethanolamide | 3.3% |
| polyacrylic acid triethanolamine salt | 0.3% |
| zinc pyridium-1-thiol-N-oxide | 1.1% |
| VEP-2 | 1.0% |
| magnesium salt of (ascorbic acid)-2-phosphate | 1.0% |
| sodium salt of (ascorbic acid)-2-phosphate | 1.0% |
| pigment | trace |
| perfume | 0.5% |
| purified water | balance |

Example B-11

A rinse was produced by the customary procedure in accordance with the following recipe:

| | |
|---|---|
| stearyldimethylbenzylammonium chloride | 1.4% |
| stearyl alcohol | 0.6% |
| glycerol monostearate | 1.5% |
| sodium chloride | 0.2% |
| VEP-2 | 1.0% |
| magnesium salt of (ascorbic acid)-2-phosphate | 1.0% |
| sodium salt of (ascorbic acid)-2-phosphate | 1.0% |
| purified water | balance |

Example B-12

A bath medicine was produced by the customary procedure in accordance with the following recipe:

| | |
|---|---|
| sodium bicarbonate | 35.5% |
| citric acid | 37.1% |
| polyethylene glycol | 2.1% |
| magnesium oxide | 1.1% |
| α-tocopherol | 0.5% |
| VEP-2 | 23.0% |
| magnesium salt of (ascorbic acid)-2-phosphate | 1.0% |
| sodium salt of (ascorbic acid)-2-phosphate | 1.0% |
| pigment | trace |
| perfume | 2.0% |

Example B-13

A toilet water was produced by the customary procedure in accordance with the following recipe:

| | |
|---|---|
| ethyl alcohol | 39.6% |
| 1,3-butylene glycol | 9.5% |
| castor oil | 4.9% |
| VEP-2 | 1.0% |
| ascorbic acid glucoside | 1.0% |
| kojic acid | 1.0% |
| placenta extract | 1.0% |
| arbutin | 1.0% |
| methyl paraben | 0.2% |
| purified water | balance |

Example B-14

A toilet water was produced by the customary procedure in accordance with the following recipe:

| | |
|---|---|
| ethyl alcohol | 39.6% |
| 1,3-butylene glycol | 9.5% |
| castor oil | 4.9% |
| VEP-5 | 3.0% |
| methyl paraben | 0.2% |
| purified water | balance |

Example B-15

A milky lotion was produced by the customary procedure in accordance with the following recipe:

| | |
|---|---|
| avocado oil | 11.0% |
| behenyl alcohol | 0.6% |
| stearic acid | 0.4% |
| glycerol fatty acid ester | 0.9% |
| polyoxyethylene sorbitan fatty acid ester | 1.1% |
| polyoxyethylene alkyl ether | 0.4% |
| VEP-5 | 3.0% |
| 1,3-butylene glycol | 10.1% |
| methyl paraben | 0.2% |
| perfume | 0.4% |
| purified water | balance |

Example B-16

A cream was produced by the customary procedure in accordance with the following recipe:

| | |
|---|---|
| squalane | 11.1% |
| stearic acid | 7.8% |
| stearyl alcohol | 6.0% |
| bees wax | 1.9% |
| propylene glycol monostearate | 3.1% |
| polyoxyethylene cetyl ether | 1.1% |
| VEP-1 | 1.0% |
| VEP-2 | 2.0% |
| 1,3-butylene glycol | 11.9% |
| methyl paraben | 0.2% |
| perfume | 0.4% |
| purified water | balance |

Example B-17

A pack was produced by the customary procedure in accordance with the following recipe:

| | |
|---|---|
| polyvinyl alcohol | 14.5% |
| sodium salt of carboxymethylcellulose | 4.8% |
| 1,3-butylene glycol | 2.9% |
| VEP-1 | 3.0% |
| ethyl alcohol | 10.0% |
| methyl paraben | 0.1% |
| purified water | balance |

Example B-18

A lip color was produced by the customary procedure in accordance with the following recipe:

| | |
|---|---|
| castor oil | 45.3% |
| hexadecyl alcohol | 25.2% |
| lanolin | 3.9% |
| bees wax | 4.8% |
| ozokerite | 3.4% |
| candelilla wax | 6.2% |
| carnauba wax | 2.1% |
| methyl paraben | 0.1% |

| | |
|---|---|
| VEP-1 | 2.0% |
| VEP-2 | 1.0% |
| titanium oxide | 2.1% |
| red pigment | 4.8% |
| perfume | 0.1% |
| water | balance |

Example B-19

A foundation was produced by the customary procedure in accordance with the following recipe:

| | |
|---|---|
| liquid paraffin | 23.5% |
| isopropyl palmitate | 14.3% |
| lanolin alcohol | 1.8% |
| lanolin acetate | 2.9% |
| microcrystalline wax | 6.5% |
| ozokerite | 7.7% |
| candelilla wax | 0.4% |
| methyl paraben | 0.1% |
| VEP-4 | 3.0% |
| titanium oxide | 14.5% |
| kaolin | 13.9% |
| talc | 5.7% |
| color pigment | 3.9% |
| perfume | 0.5% |
| water | balance |

Example B-20

A tooth paste was produced by the customary procedure in accordance with the following recipe:

| | |
|---|---|
| secondary calcium phosphate dihydrate | 45.5% |
| sodium salt of carboxymethylcellulose | 0.5% |
| carrageenan | 0.5% |
| glycerol | 9.8% |
| sorbitol | 9.7% |
| saccharin sodium | 0.1% |
| sodium lauryl sulfate | 2.3% |
| sodium chloride | 2.1% |
| α-tocopherol | 0.4% |
| VEP-3 | 1.0% |
| antiseptic | 0.1% |
| perfume | 0.5% |
| purified water | balance |

Example B-21

A gargle was produced by the customary procedure in accordance with the following recipe:

| | |
|---|---|
| ethyl alcohol | 34.6% |
| glycerol | 14.5% |
| α-tocopherol | 0.4% |
| VEP-3 | 1.0% |
| perfume | 0.1% |
| purified water | balance |

Example B-22

A hair grower was produced by the customary procedure in accordance with the following recipe:

| | |
|---|---|
| ethyl alcohol | 60.0% |
| castor oil | 4.3% |
| resorcinol | 0.7% |
| methyl paraben | 0.1% |
| capsicum tincture | 0.4% |
| α-tocopherol | 0.5% |
| VEP-4 | 0.5% |
| purified water | balance |

Example B-23

A shampoo was produced by the customary procedure in accordance with the following recipe:

| | |
|---|---|
| lauryl acid triethanolamine | 15.0% |
| lauric acid diethanolamide | 3.3% |
| polyacrylic acid triethanolamine salt | 0.3% |
| zinc pyridium-1-thiol-N-oxide | 1.1% |
| VEP-6 | 0.1% |
| VEP-1 | 0.4% |
| pigment | trace |
| perfume | 0.5% |
| purified water | balance |

Example B-24

A rinse was produced by the customary procedure in accordance with the following recipe:

| | |
|---|---|
| stearyldimethylbenzylammonium chloride | 1.4% |
| stearyl alcohol | 0.6% |
| glycerol monostearate | 1.5% |
| sodium chloride | 0.2% |
| VEP-5 | 1.0% |
| purified water | balance |

Example B-25

A bath medicine was produced by the customary procedure in accordance with the following recipe:

| | |
|---|---|
| sodium bicarbonate | 35.5% |
| citric acid | 37.1% |
| polyethylene glycol | 2.1% |
| magnesium oxide | 1.1% |
| α-tocopherol | 0.5% |
| VEP-4 | 25.0% |
| pigment | trace |
| perfume | 2.0% |

Comparative Examples B-1 to B-3

The effects of the present invention have been demonstrated by the following Comparative Examples.

A six-month stability test at 40° C. was conducted for each of the cosmetics, i.e., the VEP-2 containing cosmetic preparations of Examples B-1 to B-3 for ascertaining the effects of the present invention and corresponding control preparations (Comparative Examples) in which reagent produced by the prior art process, namely, (±)-DL-tocopheryl phosphate (produced by Sigma, containing 19% by weight of P,P'-bistocopheryl diphoshate) was used in place of VEP-2 of the present invention, these preparations having, added thereto, 0.3% of nonionic surfactant POE (20) sorbitan monooleate.

The results were evaluated on the following criteria. Namely, 1 mark was given when precipitation occurred to thereby render practical use of the preparation difficult; 2 marks were given when slight precipitation occurred but the preparation could still serve practical use; 3 marks were given when precipitation scarcely occurred; and 4 marks were given when precipitation did not occur at all. 20 observers participated in the evaluation and their marks were totaled and averaged to thereby obtain simple averages, which are listed in Table 2.

These comparative test results have demonstrated that, as apparent from the following table, the cosmetic preparations containing VEP-2 (sodium salt of dl-α-tocopheryl phosphate) of the present invention realize magnificent suppression of precipitation as compared with the controls (comparative examples) to thereby provide tocopheryl phosphate containing cosmetics which are free from precipitation even when stored for a prolonged period of time.

TABLE 2

| Tested cosmetic | Evaluation marks in precipitation test (ave. of 20 observers' marks) |
|---|---|
| Example B-1 | 3.2 |
| corresp'g Comp. Ex. | 0.7 |
| Example B-2 | 3.7 |
| corresp'g Comp. Ex. | 0.6 |
| Example B-3 | 3.1 |
| corresp'g Comp. Ex. | 0.5 |

Analytical Example 1

20 μl of a solution obtained by dissolving in an eluate 20 mg of a toilet water whose formulation was the same as in Example B-1 except that only VEP-2 was removed and to which 1% of (±)-DL-tocopheryl phosphate (produced by Sigma) was added was injected in an analytical instrument including a column packed with a gel of a polymethacrylate having, bonded thereto, octadecyl groups (Shodex RS pak D18-613 of 6 mm in diameter and 150 mm in length) and a spectrophotometrical detector for ultraviolet and visible region, and an analysis was conducted. It was found that clearly separate peaks were obtainable, one assigned to tocopheryl phosphate and the other assigned to P,P'-bistocopheryl diphoshate, so that their contents could be determined. The resultant chromatogram is shown in FIG. 2.

It was confirmed that, in FIG. 2, the peak A should be assigned to tocopheryl phosphate and the peak B should be assigned to P,P'-bistocopheryl diphoshate by the use of tocopheryl phosphate and P,P'-bistocopheryl diphoshate which were identified by $^{31}$P-NMR.

The concentrations of tocopheryl phosphate and P,P'-bistocopheryl diphoshate were 0.8% and 0.2%, respectively.

The chromatographic analysis was conducted under the following conditions:

Eluate: MeOH (methanol)/H$_2$O of 100/1 in volume ratio (containing 0.05 mol of CH$_3$COONa per liter of the total of methanol and H$_2$O), Elution rate: 0.5 ml/min, Spectrophotometer for ultraviolet and visible region: 875-UV manufactured by Japan Spectroscopic Co., Ltd., Detection wavelength: 287 nm, and Column temperature: 40° C.

Analytical Example 2

The highly purified sodium salt of dl-α-tocopheryl phosphate obtained in Example A-1 was analyzed under the same conditions as in the above Analytical Example 1, thereby obtaining a chromatogram of FIG. 3.

In FIG. 3, the peak C was assigned to sodium salt of tocopheryl phosphate. The amount of P,P'-bistocopheryl diphoshates was below the detection limit.

Analytical Example 3

20 mg of the toilet water of Example B-1 containing 1% of the highly purified sodium salt of dl-α-tocopheryl phosphate (VEP-2) according to the present invention was analyzed under the same conditions as in the above Analytical Example 1. Only the peak assigned to tocopheryl phosphate was observed as in the above Analytical Example 2. The amount of P,P'-bistocopheryl diphoshates was below the detection limit.

We claim:

1. A highly purified tocopheryl phosphate and/or a salt thereof wherein a P,P'-bistocopheryl diphoshate and/or a salt thereof is contained in a proportion of not higher than 3% by weight based on the weight.

2. The highly purified tocopheryl phosphate and/or salt thereof as claimed in claim 1, wherein the proportion of the P,P'-bistocopheryl diphoshate and/or salt thereof is not higher than 0.5% by weight based on the weight.

3. A highly purified tocopheryl phosphate and/or salt thereof, wherein an aqueous solution formed therefrom having a concentration of 3% by weight with a pH value of 8.5, is clear or substantially clear.

4. The highly purified tocopheryl phosphate and/or salt thereof as claimed in any of claims 1 to 3, wherein the salt of tocopheryl phosphate contained therein is present in the form of a sodium salt or a potassium salt.

5. A process for producing a highly purified tocopheryl phosphate and/or a salt thereof, which comprises hydrolyzing under acid condition a mixture of:

a tocopheryl phosphate and/or a salt thereof (i) and a P,P'-bistocopheryl diphoshate and/or a salt thereof (ii).

6. A process for producing a highly purified tocopheryl phosphate and/or a salt thereof, which comprises the steps of:

reacting a tocopherol with an oxyphosphorus trihalide and treating the reaction mixture with an acid or basic aqueous solution to thereby form a tocopheryl phosphate and/or a salt thereof in which a P,P'-bistocopheryl diphoshate and/or a salt thereof formed as a by-product is contained, hydrolyzing the P,P'-bistocopheryl diphoshate and/or salt thereof under acid condition, and, optionally, rendering the hydrolyzate neutral or basic under basic condition.

* * * * *